United States Patent [19]

Tamura et al.

[11] Patent Number: 4,645,754

[45] Date of Patent: Feb. 24, 1987

[54] SILVER CATALYST FOR PRODUCTION OF ETHYLENE OXIDE AND METHOD FOR MANUFACTURE THEREOF

[75] Inventors: Fumihide Tamura, Yokohama; Minoru Saotome, Ebina, both of Japan

[73] Assignee: Nippon Shokubai Kagaku Kogyo Co., Ltd., Osaka, Japan

[21] Appl. No.: 786,329

[22] Filed: Oct. 10, 1985

[51] Int. Cl.$^4$ .................. B01J 31/00; B01J 21/18; B01J 27/055; B01J 2/08

[52] U.S. Cl. ..................... 502/527; 502/152; 502/167; 502/174; 502/201; 502/218; 502/243; 502/347; 502/348

[58] Field of Search ............... 502/152, 167, 174, 201, 502/218, 243, 347, 348, 527

[56] References Cited

U.S. PATENT DOCUMENTS

| | | | |
|---|---|---|---|
| 2,408,164 | 9/1946 | Foster | 502/527 X |
| 2,639,909 | 5/1953 | Leva | 502/527 X |
| 3,065,595 | 11/1962 | Cory | 423/213.2 X |
| 3,563,914 | 2/1971 | Wattemena | 502/348 |
| 3,764,565 | 10/1973 | Jacobs et al. | 502/527 X |
| 3,892,679 | 7/1975 | Holler | 502/347 |
| 3,898,180 | 8/1975 | Crooks et al. | 502/527 X |
| 3,962,136 | 6/1976 | Nielsen et al. | 502/347 X |
| 3,972,830 | 8/1976 | Bryce-Smith et al. | 502/167 |
| 4,010,115 | 3/1977 | Neilsen et al. | 502/243 |
| 4,033,903 | 7/1977 | Maxwell | 502/347 |
| 4,097,414 | 6/1978 | Canitt | 502/347 |
| 4,123,385 | 10/1978 | Rebsdot et al. | 502/348 X |
| 4,168,247 | 9/1979 | Hayden et al. | 502/347 |
| 4,212,772 | 7/1980 | Mross et al. | 502/347 |
| 4,242,235 | 12/1980 | Cognion et al. | 502/243 |
| 4,278,562 | 7/1981 | Mross et al. | 502/167 X |
| 4,342,667 | 8/1982 | Armstrong et al. | 502/347 |
| 4,400,308 | 8/1983 | Alter et al. | 502/347 X |
| 4,458,032 | 7/1984 | Rebsdot et al. | 502/347 X |
| 4,471,071 | 9/1984 | Rebsdot et al. | 502/348 X |

FOREIGN PATENT DOCUMENTS

| | | | |
|---|---|---|---|
| 2448449 | 4/1975 | Fed. Rep. of Germany | 502/348 |
| 2783359 | 6/1979 | Fed. Rep. of Germany | 502/243 |
| 5764621 | 7/1980 | Japan | 502/201 |
| 59-196743 | 11/1984 | Japan | 502/243 |
| 2002252A | 2/1979 | United Kingdom | 502/347 |
| 2044481A | 10/1980 | United Kingdom | 502/243 |

Primary Examiner—Andrew H. Metz
Assistant Examiner—William G. Wright
Attorney, Agent, or Firm—Omri M. Behr

[57] ABSTRACT

A silver catalyst for the production of ethylene oxide by catalytic vapor phase oxidation of ethylene with molecular oxygen in the presence of a halogenated inhibitor, having silver and at least one accelerator selected from the group consisting of alkali metals and alkali metal compounds deposited on a porous inorganic refractory carrier in the shape of Intalox saddles or Berl saddles, and the method for manufacture thereof.

28 Claims, 12 Drawing Figures

SILVER CATALYST FOR PRODUCTION OF ETHYLENE OXIDE AND METHOD FOR MANUFACTURE THEREOF

BACKGROUND OF THE INVENTION

1. Field of the Invention

This invention relates to a silver catalyst to be used in the production of ethylene oxide by catalytic vapor phase oxidation of ethylene with molecular oxygen in the presence of a halogenated inhibitor and to a method for the manufacture of the silver catalyst.

2. Description of Prior Art

The silver catalyst which is used in commercial production of ethylene oxide by catalytic vapor phase oxidation of ethylene with molecular oxygen is required to exhibit high selectivity and high activity in performance, keep high selectivity and high activity for a long period, and suffer only minimal pressure loss in catalyst bed.

Various studies have been made to date for the purpose of improving the catalyst properties and fulfilling the requirements and numerous efforts have been directed to improving carriers, reaction accelerators, and silver compounds. Attempts at improvement of the method of silver deposition are disclosed in Japanese Patent Publication SHO 46(1971)-19,606, U.S. Pat. No. 3,702,259, Japanese Patent Publication No. SHO 59(1984)-29,291, U.S. Pat. No. 4,248,740, U.S. Pat. No. 4,305,844, and U.S. Pat. No. 4,400,308.

As regards reaction accelerators, it has been held that mainly alkali metals and thallium are effective. Various proposals have been made on kinds and amounts of elements and on methods of incorporation as in the specifications of U.S. Pat. No. 3,962,136, U.S. Pat. No. 4,039,561, U.S. Pat. No. 4,207,210, Japanese Patent Laid-open No. SHO 50(1975)-95,213, U.S. Pat. No. 3,962,136, U.S. Pat. No. 4,033,903, U.S. Pat. No. 4,248,740, UK Patent Application No. 2,043,481, and Japanese Patent Laid-oepn No. SHO 56(1981)-5,471, U.S. Pat. No. 4,389,338, for example.

Numerous reports have been proposed on carriers. They appear in the U.S. Pat. No. 3,207,700, Japanese Patent Publication No. SHO 43(1968)-13,137, Japanese Patent Publication No. SHO 45(1970)-21,373, Japanese Patent Publication No. SHO 45(1970)-22,419, Japanese Patent Publication No. SHO 45(1970)-11,217, U.S. Pat. No. 4,368,144, U.S. Pat. No. 2,766,261, U.S. Pat. No. 3,172,893, U.S. Pat. No. 3,664,970, and U.S. Pat. No. 4,242,235. Many of these reports concern pore size distribution and specific surface area of carrier.

Further, U.S. Pat. No. 3,664,970 discloses saddles as the carrier, but the catalyst prepared by using such carrier is appropriate for unprovid oxidation of ethylene in the absence of halogenated inhibitor.

All these specifications make no mention of improvement in selectivity of catalysis or pressure performance of catalyst bed due to selection of the shape of carrier but merely go the length of disclosing pellets, spheres, and Raschig rings, i.e. the shapes of catalysts preponderantly adopted to date on commercial scale.

U.S. Pat. No. 4,389,338 discloses a method for the preparation of a silver catalyst by the steps of depositing silver and an alkali metal and/or thallium as reaction accelerators on a porous inorganic refractory carrier and subjecting the resultant composite to a high temperature treatment in an inert gas having a final oxygen content of not more than 3% by volume at elevated temperatures in the range of 550° to 950° C.

In the specification of U.S. Pat. No. 4,248,740 is disclosed a method which produces a silver catalyst by impregnating a porous inorganic refractory carrier with a silver compound solution containing a reducing compound, subjecting the impregnated carrier to a heat treatment for reduction thereby causing metallic silver to be dispersed and deposited on the surface of the carrier and on the inner surface of fine pores in the carrier, then washing the composite with water and/or lower alcohol, drying the washed composite, impregnating the dried composite with a solution containing an alkali metal and/or alkali metal compound, and drying the impregnated composite through vaporization of the liquid component. These are examples of the methods for the production of commercially available silver catalysts possessed of catalyst properties combining the highest selectivity, the highest activity, and keep the highest selectivity and the highest activity for the longest period. They, however, are not fully satisfactory in selectivity.

Concerning carriers for silver catalysts used in the production of ethylene oxide, many points remain yet to be elucidated and many problems remain yet to be solved. For example, physical properties such as combination of components for carrier, specific surface area, pore diameter, pore distribution, pore volume, porosity, grain size, and shape of carrier and chemical properties possessed by such carrier materials as α-alumina, silicon carbide, silica, and zirconia await improvement for optimization.

An object of this invention, therefore, is to provide a novel silver catalyst for the proudction of ethylene oxide which catalyst is used in the production of ethylene oxide by catalytic vapor phase oxidation of ethylene with molecular oxygen in the presence of a halogenated inhibitor and a method for the manufacture of the silver catalyst.

Another object of this invention is to provide a silver catalyst which permits production of ethylene oxide from ethylene and molecular oxygen in the presence of a halogenated inhibitor with high selectivity and which suffers only minimal pressure loss in catalyst bed and a method for the manufacture of the silver catalyst.

SUMMARY OF THE INVENTION

The objects described above are accomplished by a silver catalyst for the production of ethylene oxide by catalytic vapor phase oxidation of ethylene with molecular oxygen in the presence of a halogenated inhibitor, which has silver and at least one accelerator selected from the group consisting of alkali metals and alkali metal compounds deposited on a porous inorganic refractory carrier in the form of Intalox saddles or Berl saddles.

Further, in a method for the manufacture of a silver catalyst having fine silver particles dispersed and deposited on the outer surface of a porous inorganic refractory carrier and on the inner wall surface of fine pores in the carrier and used in the production of ethylene oxide by catalytic vapor phase oxidation of ethylene with molecular oxygen in the presence of a halogenated inhibitor, the objects are accomplished by the method which is characterized by depositing silver and at least one accelerator selected from the group consisting of alkali metals and alkali metal compounds on a porous inorganic refractory carrier in the shape of Intalox saddles or Berl saddles and finally subjecting the resultant composite to a high temperature treatment in an inert gas having an oxygen content of not more than 3% by volume at elevated temperatures in the range of 550° to 950° C.

In a method for the manufacture of a silver catalyst having fine silver particles dispersed and deposited on the outer surface of a porous inorganic refractory carrier and on the inner wall surface of fine pores in the carrier and used in the production of ethylene oxide by catalytic vapor phase oxidation of ethylene with molecular oxygen in the presence of a halogenated inhibitor, the objects are accomplished by the method which is characterized by impregnating a porous inorganic refractory carrier in the shape of Intalox saddles or Berl saddles with a silver compound solution containing a reducing compound, heating the impregnated carrier for reduction thereby dispersing and depositing metallic silver on the outer surface of the carrier and on the inner surface of pores in the carrier, subsequently washing the resultant composite with at least one liquid selected from the group consisting of water and lower alcohols, drying the wet composite, impregnating the dried composite with a solution containing at least one member selected from the group consisting of alkali metals and alkali metal compounds, and drying the wet composite thereby expelling the liquid component through vaporization.

We have made a study on the shape of a carrier suitable for use in an silver catalyst for the production of ethylene oxide. They have consequently found that when a porous inorganic refractory carrier in the shape of Intalox saddles or Berl saddles is used in the place of the conventional carrier in the shape of spheres or Raschig rings used prevalently in silver catalysts currently finding utility on commercial scale in the art, there is obtained a catalyst which enjoys heretofore unattainable high selectivity and suffers only minimal pressure loss in catalyst bed. The present invention has been produced based on this discovery.

In the production of ethylene oxide by catalytic vapor phase oxidation of ethylene with molecular oxygen in the presence of a halogenated inhibitor, a silver catalyst is used. Virtually all silver catalysts available for this purpose are naturally carried catalysts using carriers of their own. It is also known well that the carriers used therefor are porous granular refractories.

Although they may be generalized by the simple term of "porous granular refractory carrier," they are widely varied in such physical properties as specific surface area, pore distribution, pore volume, grain size, and shape of carrier and such chemical properties as possessed by materials for carrier including α-alumina, silica, silicon carbide, zirconia, and clay. These physical properties and chemical properties have conspicuous effects on the properties of catalyst.

Selection of a particular carrier from among numerous carriers possessed of a varying set of properties, therefore, is an important problem to persons skilled in the art. Particularly, the shape of carrier heavily affects the properties of catalyst. In the manufacture of a catalyst, specifically in the step for deposition of silver and an alkali metal and/or an alkali metal compound, the selection of a carrier shape capable of readily enabling the deposition to be uniformly effected leads to production of a catalyst excelling in selectivity. Further, the selection of a carrier shape such that, during the course of a reaction, stagnation of gas in the catalyst particles will not easily effected constitutes a key for successful production of a catalyst excelling in selectivity. In this respect, the ratio of the apparent surface area of the catalyst to the apparent volume (exclusive volume) is desired to be large. Most carriers heretofore adopted on commercial scale are in the shape of spheres or Raschig rings. In the spheres, an increase in this ratio is attained by decreasing their particle diameter. If their particle diameter is excessively decreased, however, the spheres during the reaction suffer from a very large pressure loss. Thus, such excessive decrease of particle diameter proves detrimental in terms of both equipment and utilities. In the Raschig rings, a decrease in their wall thickness is effective in increasing the ratio. The decrease, however, proves disadvantageous because it entails a decrease in crushing strength and a decrease in the surface area of catalyst per unit volume of reaction tube.

The statement that the selectivity of the catalyst increases in proportion as the ratio of the apparent surface area of the carrier to the apparent volume thereof increases does not always hold true. The increase of this ratio has its own upper limit.

We have studied carriers of varying shape. We have consequently found that catalysts using a porous inorganic refractory carrier in the shape of Intalox saddles or Berl saddles have high selectivity and suffer only minimal pressure loss in catalyst bed.

The porous inorganic refractory carrier in the shape of Intalox saddles or Berl saddles has a lower packing specific gravity for fixed grain size and wall thickness than Raschig rings. This is equivalent to a statement that the surface area of catalyst per unit volume of the reaction tube decreases. It is a surprising fact that the catalyst, despite its apparently disadvantageous shpae, exhibits satisfactory selectivity and suffers low pressure loss in catalyst bed. Even when the ratio of apparent suface area to apparent volume in a catalyst using a carrier in the shape of spheres or Raschig rings is equalized with that in a catalyst using a porous inorganic refractory carrier in the shape of Intalox saddles or Berl saddles, the former catalyst does not acquire so high selectivity and so low pressure loss as attained by the latter catalyst. Further when the packing specific gravity in a catalyst using a carrier in the shape of spheres or Raschig rings is equalized with that in a catalyst using a porous inorganic refractory carrier in the shape of Intalox saddles or Berl saddles, the former catalyst does not acquire so high selectivity and so low pressure loss as attained by the latter catalyst.

DESCRIPTION OF PREFERRED EMBODIMENT

Figure 1:
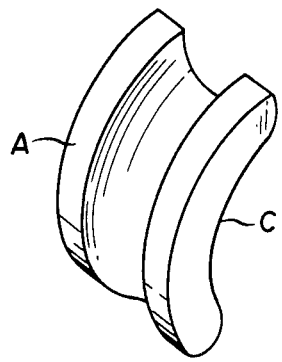
FIG. 1 is a perspective view of an Intalox saddle carrier.

The porous inorganic refractory carrier of this invention in the shape of Intalox saddles or Berl saddles effectively has a specific surface area in the range of 0.01 to 10 m$^2$/g, preferably 0.1 to 5 m$^2$/g. If the specific surface area is less than 0.01 m$^2$/g, the porous inorganic refractory carrier in the shape of Intalox saddles or Berl saddles has such a small packing specific gravity that the surface area per unit volume of reaction tube is extremely small and the carrier proves disadvantageous in terms activity. If the specific surface area exceeds 10 m$^2$/g, the pore diameter in the carrier is so small that the reactant gas and the resultant gas tend to stagnage within the particles of the catalyst during the reaction. The ratio of apparent surface area to apparent volume in the porous inorganic refractory carrier in the shape of Intalox saddles or Berl saddles which is used in this invention is in the range of 0.1 to 10 mm$^{-1}$, preferably 0.5 to 5 mm$^{-1}$. If the ratio of apparent surface area to apparent volume is less than 0.1 mm$^{-1}$, the selectivity to ethylene oxide brings down. If the ratio of apparent surface area to apparent volume exceeds 10 mm$^{-1}$, the Intalox saddles or Berl saddles have too small a thickness to retain the strength required for any industrial catalysts.

The physical properties of the porous inorganic refractory carrier in the shape of Intalox saddles are desired to be such that the apparent porosity will fall in the range of 20 to 80%, preferably 30 to 70%, the specific pore volume in the range of 0.06 to 1.0 cc/g, preferably 0.1 to 0.8 cc/g, the outer peripheral length (A) in the range of 3 to 70 mm, preferably 3.5 to 30 mm, the inner peripheral length (C) in the length of 1.5 to 68 mm, preferably 1.8 to 28 mm, the thickness (W) in the range of 0.1 to 4 mm, preferably 0.8 to 3 mm, the outside diameter (D) in the range of 0.5 to 20 mm, preferably 3 to 15 mm, and the length (E) in the range of 0.5 to 65 mm, preferably 3 to 20 mm.

The physical properties of the porous inorganic refractory carrier in the shape of Berl saddles are desired to be such that the apparent porosity will fall in the range of 20 to 80%, preferably 30 to 70%, the specific pore volume in the range of 0.06 to 1.0 cc/g, preferably 0.1 to 0.8 cc/g, the outer peripheral length (A) in the range of 3 to 70 mm, preferably 3.5 to 30 mm, the inner peripheral length (C) in the range of 1.5 to 68 mm, preferably 1.8 to 28 mm, the thickness (W) in the range of 0.1 to 4 mm, preferably 0.8 to 3 mm, the outside diameter (D) in the range of 0.5 to 20 mm, preferably 3 to 15 mm, and the length (E) in the range of 0.5 to 65 mm, preferably 3 to 20 mm.

Exampels of the the suitable material for the carrier are $\alpha$-alumina, silicon carbide, silica, zirconia, and clay. In the substances cited above, $\alpha$-alumina is the best selection. Further, the component which is incorporated in the carrier in addition to the main comonent is desired to be in an amount approximating the amount generally accepted as common in the art.

Figure 2:
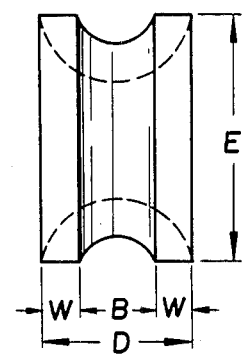
FIG. 2 is a front view of the Intalox saddle carrier.
Figure 3:
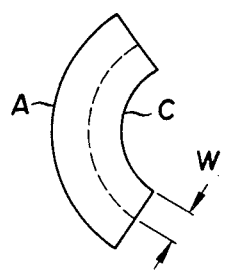
FIG. 3 is a side view of the Intalox saddle carrier.
Figure 4:
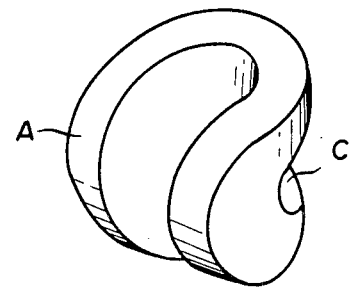
FIG. 4 is a perspective view of a Berl saddle carrier.
Figure 5:
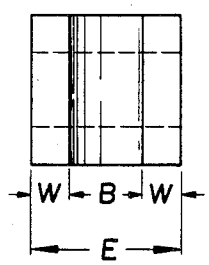
FIG. 5 is a front view of the Berl saddle carrier.
Figure 6:
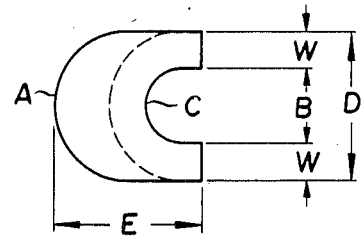
FIG. 6 is a side view of the Berl saddle carrier.

Examples of the shape of the carrier used in the present invention are shown in the drawings. FIGS. 1-3 depict a porous inorganic refractory carrier in the shape of an Intalox saddle and FIGS. 4-6 depict a porous inorganic refractory carrier in the shape of a Berl saddle.

For the preparation of the carrier, any of the conventional methods which are available for the purpose can be used. Generally, the method which effects this preparation by impregnating the carrier with an aqueous solution or an organic solvent solution of a decomposable silver salt such as, for example, aqueous silver nitrate solution, an ammonia solution of silver salt of an inorganic or organic acid, an organic acid amine solution, or an aqueous silver lactate solution is adopted. Optionally, an alkali metal and/or an alkali metal compound may be preparatorily deposited on the carrier, may be added to a silver solution and subsequently deposited simultaneously with silver on the carrier, or may be deposited on the carrier on which silver has already been deposited in consequence of the step of decomposition and reduction of silver and the subsequent step of decomposition and removal. Thereafter, the method which comprises heating the impregnated carrier thereby decomposing or reducing the decomposable silver salt and subsequently decomposing and removing the product of decomposition with a heated gas or the method which comprises removing the product of decomposition with water or an organic solvent thereby producing a catalyst may be adopted.

The silver catalyst of this invention using a porous inorganic refractory carrier in the shape of Intalox saddles or Berl saddles, e.g. the silver catalyst to be used for the production of ethylene oxide by catalytic vapor phase oxidation of ethylene with molecular oxygen in the presence of a halogenated inhibitor, is prepared by the method which comprises impregnating a porous inorganic refractory carrier in the shape of Intalox saddles or Berl saddles with a decomposable sivler solution such as an amine solution of silver salt or an organic acid, then heating the impregnated carrier at a temperature in the range of 100° to 300° C. thereby reducing or thermally decomposing the silver salt, and decomposing and removing the resultant product of decomposition with a heated gas or removing the decomposition product with a solvent.

Other examples of the method usable for the preparation of the silver catalyst are as follows.

(1) A method for the manufacture of a silver-deposited catalyst for the production of ethylene oxide, which comprises impregnating porous inorganic carrier in the shape of Intalox saddles or Berl saddles with a mixed solution containing silver nitrate, at least one member selected from the group consisting of lower aliphatic alcohols of 2 to 6 carbon atoms possessing 1 to 3 alcoholic hydroxyl groups in the molecular unit or at least one member selected from the group consisting of lower aliphatic alcohols of 2 to 6 carbon atoms possessing 1 to 3 alcoholic hydroxyl groups in the molecular unit and water, and at least one member selected from the group consisting of lower acid amides of 1 to 4 carbon atoms, then heating the impregnated carrier thereby effecting deposition of metallic silver on the carrier, and further heating the resultant composite thereby removing organic substances therefrom.

(2) A method for the manufacture of a silver catalyst for use in the production of ethylene oxide, which comprises causing silver and alkali metal and/or an alkali metal compound to be deposited on a porous inorganic refractory carrier in the shape of Intalox saddles or Berl saddles and finally subjecting the resultant composite to a high temperature treatment in an inert gas having an oxygen content of not more than 3% by volume at elevated temperatures in the range of 550° to 950° C.

(3) A method for the manufacture of a silver catalyst for use in the production of ethylene oxide, which comprises impregnating a porous inorganic refractory carrier in the shape of Intalox saddles or Berl saddles with a silver compound solution containing a reducing compound, subjecting the impregnated carrier to a thermal reducing treatment thereby effecting dispersion and deposition of metallic silver on the outer surface of the carrier and on the inner surface of fine pores in the carrier, washing the resultant composite with water and/or a lower alcohol, drying the wet composite, then impregnating the dried composite with a solution containing an alkali metal and/or an alkali metal compound, and drying the impregnated composite thereby expelling the liquid component by vaporiazation.

On the inner and outer surfaces of the carrier, silver can be deposited in the form of fine particles in an amount of 5 to 30% by weight, preferably 5 to 25% by weight, based on the catalyst. The alkali metal or alkali metal compound is one or more members selected from the group consisting of metals and compound is added in the form of an aqueous solution or an alcoholic solution in an amount in the range of 0.0001 to 0.05 gram equivalent, preferably not less than 0.001 gram equivalent and not more than 0.03 gram equivalent, based on 1 kg of the completed catalyst to the silver solution and is deposited on the carrier simultaneously with silver. Alternatively, the alkali metal or alkali metal compound may be deposited on the carrier either before or after deposition of silver thereon.

For the preparation of the catalyst of the present invention, the method (2) or (3) proves particularly desirable.

In the method (2) for the manufacture of the catalyst of this invention, the portion of the procedure up to the step of high temperature treatment can be performed by using any of most methods heretofore known in the art. A procedure which comprises impregnating a porous inorganic refractory carrier in the shape of Intalox saddles or Berl saddles with an aqueous solution an organic solvent solution of an organic or inorganic silver salt such as, for example, an aqueous silver lactate solution or an organic amine solution of silver salt of an organic acid and an aqueous solution or an orgainc solvent solution of an alkali metal and/or an alkali metal compound such as, for example, an aqueous cesium nitrate solution, an aqueous cesium carbonate solution, or an alcohol solution of cesium carbonate, drying the impregnated carrier, heating the dried carrier thereby decomposing or reducing the silver salt and effecting deposition of metallic silver and an alkali metal and/or an alkali metal compound on the carrier, and further heating the resultant composite for the purpose of activation, i.e. for thermally decomposing and diffusing excess organic or inorganic component and producing a catalyst and a procedure which comprises impregnating a porous inorganic refractory carrier in the shape of Intalox saddles or Berl saddles with an aqueous solution or an organic solvent solution of an organic or inorganic silver salt such as, for example, an aqueous silver lactate solution or an organic amine solution of silver salt of an organic acid, drying the impregnated carrier, heating the dried carrier thereby decomposing or reducing the silver salt and effecting deposition of the metallic silver on the carrier, subsequently subjecting the resultant composite to the so-called activation, i.e. removing excess organic or inorganic component by washing with water or an organic solvent or by boiling, then impregnation the resultant composite with an aqueous solution or an organic solvent solution of an alkali metal and/or an alkali metal compound such as, for example, an aqueous cesium nitrate solution or an aqueous cesium carbonate or an alcohol solution of cesium carbonate, and drying the impregnated composite and producing a catalyst are examples. As the silver salt solution to be used in either of the procedures cited above, any of virtually all the silver salt solutions known to the art can be adopted. Examples of the silver salt solutions advantageously usable therefor include aqueous solutions of silver nitrate and silver lactate, amine solutions of silver oxalate, silver acetate, and silver carbonate, and glycol solutions of silver nitrate. Thus, silver can be deposited in the form of fine particles on the inner and outer surfaces of the carrier in an amount of 5 to 30% by weight, preferably 5 to 25% by weight, based on the catalyst.

As the alkali metal or alkali metal compound, one or more members selected from the group consisting of metals and compounds of potassium, rubidium, and cesium, preferably cesium. Examples of the compound advantageously usable herein are nitrates, sulfates, hydroxides, oxides, and acetates. Such a compound is used in the form of an aqueous solution or a methanol, ethanol, or other similar alcoholic solution. The alkali metal or the alkali metal compound can be added in an amount in the range of 0.001 to 0.05 gram equivalent, preferably not less than 0.003 gram equivalent and not more than 0.03 gram equivalent, per 1 kg of the completed catalyst to the silver solution and deposited simultaneously with silver on tne carrier. Alternatively, it can be deposited on the carrier either before or after deposition of silver thereon.

The activation treatment involved in the present invention can be effected by any of the conventional methods adapted in the art. For example, it can be carried out by thermal decomposition in air or in an inert gas at temperatures in the range of about 150° to 400° C., though variable with the kinds of silver salt and solvent to be used. The thermal decomposition of an aqueous silver lactate solution or an amine solution of silver salt of an organic acid may be cited as an example. Otherwise, a method of reduction with a current of hydrogen which is carried out when there is used an aqueous silver nitrate solution may be used. One special method special effects the activation by washing the composite with water or an alcohol. This and other similar methods can be utilized for this invention. In the case of the method which resorts to the washing of the composite, it should be noted that the deposition of the alkali metal or the alkali metal compound on the carrier is effected after the step of the activation by the washing.

Subsequently to the activation which is carried out as described above, the silver catalyst containing the alkali metal or the alkali metal compound is subjected to a high temperature treatment in an inert gas having an oxygen content of not more than 3% by volume, desirably not more than 1% by volume, and more desirably not more than 0.1% by volume at elevated temperatures in the range of 550° to 950° C.

Examples of the inert gas advantageously usable in this high temperature treatment include nitrogen, helium, argon, carbon dioxide, and neon. The elevated temperatures at which the high temperature treatment is carried out fall in the range of 550° to 950° C., preferably 550° to 800° C.

The duration of this high temperature treatment is at least 3 minutes, preferably at least 20 minutes. The time for temperature elevation and the time for temperature fall are excluded from the duration just mentioned.

The expression "final" as used in the present invention means the period which intervenes the time the so-called activation treatment, i.e. the heat treatment performed in air or in an oxygen-containing gas at a relatively low temperature in the range of 150° to 400° C. for the purpose of decomposing and diffusing the organic component and the unwanted inorganic component thereby activating the silver compound and the reaction accelerator such as an alkali metal or an alkali metal compound used in the preparation of the catalyst by the known method, is completed and the time the catalyst produced consequently begins to deteriorate or the period which follows completion of the step of removing the unwanted organic and inorganic components by washing for the purpose of activation the silver compound used and thereafter dissolving the raction accelerator such as an alkali metal or an alkali metal compound in water or a lower alcohol, impregnating the composite with the resultant solution, and drying the impregnated composite.

As the silver compound solution containing a reducing compound which is used for the method (3) of this invention, any of all the solutions heretofore known to the art can be used. Examples of the solution effectively used for the purpose include monoethylene glycol solutions of silver nitrate containing a lower acid amide as a reducing component, solutions having a varying silver compound dissolved in an alkanol amine or other amine and containing a varying alkanol amine as a reducing compound, and an aqueous silver nitrate solution containing formalin as a reducing component.

Typical examples of the lower amide to be used as the reducing compound include formamide, acetamide, propionic acid amide, glycolic acid amide, and dimethyl formamide. Typical examples of the alkanol amine and other amine include momo-, di-, and tri-ethanol amines, mono-, di-, and tri-n-propanol amines, mono-, di-, and triisopropanol amines, n-butanol amines, and isobutanol amines. These reducing compounds exhibit a reducing activity at temperatures ranging from normal room temperature to 200° C. and convert dissolved silver compounds into metallic silver.

As the silver compound to be used as a raw material, any of the inorganic silver salts and the organic silver salts which are capable of reaction with the lower acid amide and consequently forming complex salts can be used. Typical examples of the silver compound include silver nitrate, silver carbonate, silver sulfate, silver acetate, silver lactate, silver succinate, and silver glycolate.

In the catalyst, silver can be deposited on the inner and outer surfaces of the carrier in the form of fine particles in an amount falling in the range of 5 to 30% by weight, preferably 5 to 25% by weight, based on the produced catalyst.

The solvent to be used is one member selected from the group consisting of lower aliphatic compounds of 2 to 6 carbon atoms containing 1 to 3 alcoholic hydroxyl groups in the molecular unit thereof. Typical examples of the lower aliphatic compound used advantageously particularly where a lower acid amide is used as a reducing compound include monoethylene glycol, diethylene glycol, triethylene glycol, trimethylene glycol, monopropylene glycol, methyl cellosolve, ethyl cellosolve, methyl carbitol, ethyl carbitol, and glycerin. Amines such as alkanol amines and water are other examples of the solvent usable advantageously.

As the alkali metal or alkali metal compound, one or more members selected from the group consisting of metals and compounds of potassium, rubidium, and cesium, preferably cesium can be used. Typical examples are nitrates, sulfates hydroxides, oxides, and acetates. The alkali metal or alkali metal compound described above is used in the form of an aqueous solution or a solution in methanol, ethanol, propanol or other similar lower alcohol. The alkali metal or alkali metal compound is desired to be used in an amount falling in the range of 0.0001 to 0.03 gram equivalent, preferably 0.0008 to 0.02 gram equivalent, per 1 kg of the completed catalyst.

Now, the method for manufacturing a sivler deposited catalyst using a lower acid amide as a reducing compound will be described specifically below.

Silver nitrate is dissolved in a solvent such as, for example, ethylene glycol of an amount 1 to 20 times, preferably 1 to 10 times, the weight of silver nitrate. In the resultant solution, a reducing compound such as, for example, formamide added thereto in an amount of 0.5 to 5 times, preferably 1 to 3 times, the silver component of the solution in molar ratio is thoroughly stirred. A prescribed amount of a porous inorganic refractory carrier in the shape of Intalox saddles or Berl saddles is impregnated with the resultant solution. The impregnated carrier is heated at a temperature in the range of 100° to 150° C. for 1 to 10 hours. Consequently, silver is formed by reduction and deposited in the form of fine particles on the outer surface of the carrier and on the inner surface of fine pores in the carrier.

The carrier having activated silver dispersed and deposited on the outer surface thereof and on the inner surface of fine pores therein is washed with water, preferably with boiling water. This washing is effective in removing organic substances such as formamide and ethylene glycol from within the catalyst and, at the same time, cleaning the surface of the produced activated silver and further activating the silver.

After the wahsing, the silver-deposited carrier is heated at a temperature in the range of 50° to 150° C. to be dried. The catalyst thus produced is impregnated with an aqueous solution or a methanol, ethanol, or some other similar lower alcohol solution containing a prescribed amount of a reaction accelerator. The impregnated catalyst is heated at a temperature in the range of 50° to 150° C. to expel the solvent therefrom by vaporization. Throughout all these steps, all precautions should be exercised to avoid heating the catalyst to a temperature above 200° C.

In the production of ethylene oxide by catalytic vapor phase oxidation of ethylene with molecular oxygen using the silver catalyst of the present invention, it is desirably adopted a halide such as chloride, bromide, fluoride and iodide, e.g., ethylene dichloride, vinyl chloride, chlorinated diphenyl, monochlorobenzene, and dichlorobenzene as an halogenated inhibitor in the range of 0.1 to 10 ppm (volume) as a content of reaction gas.

In the production of ethylene oxide by catalytic vapor phase oxidation of ethylene with molecular oxygen using the silver catalyst of the present invention, when the halogenated inhibitor is not used, the selectivity to ethylene oxide brings down and also the reaction temperature goes up.

In the production of ethylene oxide by catalytic vapor phase oxidation of ethylene with molecular oxygen in the presence of a halogenated inhibitor using the silver catalyst of the present invention, all conditions known to the art until now may be adopted. Conditions in general at commercial scale of the production thereof, namely the reaction temperature is in the range of 150° to 300° C., preferably 180° to 280° C., the reaction pressure in the range of 2 to 40 kg/cm² G, preferably 10 to 30 kg/cm² G, and the space velocity in the range of 1,000 to 30,000 hr$^{-1}$ (STP), preferably 3,000 to 8,000 hr$^{-1}$ (STP). The feed gas to be passed through the catalyst is composed desirably of 0.5 to 40% by volume of ethylene, 3 to 10% by volume of oxygen, 5 to 30% by volume of carbon dioxide gas, and the balance of an inert gas such as nitrogen, argon, or steam and a lower hydrocarbon such as methane or ethane.

Now, the present invention will be described more specifically below with reference to working examples and comparative experiments. This invention is not limited to the working examples so cited but may be practised otherwise without departing from the spirit of the invention disclosed herein.

The conversion and the selectivity indicated in the working examples and the comparative experiments represent the numerical values to be calculated respectively by the following formulas.

$$\text{Conversion (\%)} = \frac{\text{Number of mols of ethylene reacted}}{\text{Number of mols of ethylene in feed gas}} \times 100$$

Selectivity (%) =

$$\frac{\text{Number of mols of ethylene converted into ethylene oxide}}{\text{Number of mols of ethylene reacted}} \times 100$$

EXAMPLE 1

A slurry of 360 g of silver oxalate in 100 ml of water and 300 ml of ethanol amine added thereto were thoroughly stirred for solution. The resultant mixture and 100 ml of water added thereto were thoroughly stirred. The diluted mixture was stirred with a solution of 2.3 g of cesium nitrate in 200 ml of water to produce an impregnating solution. With this solution, 4,000 ml of a pre-heated α-alumina carrier at about 100° C. (FIGS. 1 to 3) in the shape of Intalox saddles having a apparent porosity of 55%, a BET specific surface area of 0.7 m²/g, a pore volume of 0.32 cc/g, an outside diameter (D) of 6.0 mm, a thickness (W) of 1.5 mm, an outer peripheral length (A) of 13.3 mm, an inner peripheral length (C) of 5.8 mm, and a ratio of apparent surface area to apparent volume of 1.9 mm$^{-1}$. The impregnated carrier was concentrated and dried by heating, then heated in a bath of air at 120° C. for three hours, and subsequently activated in a current of air at 280° C. for 48 hours.

The resultant catalyst was placed to pack an externally heated double-pipe stainless steel reactor 25 mm in inside diameter and 11,000 mm in pipe length. To the catalyst bed, a mixed gas comprising 20% by volume of ethylene, 7% by volume of oxygen, 7% by volume of carbon dioxide gas, and the balance of methane, nitrogen, argon, and ethane and further containing 1 ppm of ethylene dichloride was fed to effect the reaction under the conditions of 24 kg/cm² of reaction pressure, 5,500 hr$^{-1}$ of space velocity. The results are shown in Table 1.

EXAMPLE 2

A catalyst was prepared and use in the reaction by following the procedure of Example 1, except that the amount of cesium nitrate was changed to 7.0 g, the catalyst activated in a current of air at 280° C. for 48 hours was placed in a stainless steel tightly closed container capable of introducing an inert gas from outside, and the reaction was carried out under continued flow of nitrogen gas for three hours with the catalyst bed kept at 670° C. The reaction was carried out by following the procedure of Example 1. The results are shown in Table 1.

EXAMPLE 3

A catalyst was prepared by following the procedure of Example 1, except that an α-alumina carrier (FIGS. 4 to 6) in the shape of Berl saddles having an outside diameter (D) of 6.0 mm, a thickness (W) of 1.5 mm, an outer peripheral length (A) of 15.4 mm, an inner peripheral length (C) of 6.2 mm, and a ratio of apparent surface area to apparent volume of 1.9 mm$^{-1}$ was used in the place of the carrier in the shape of Intalox saddles and solution of 2.7 g of cesium nitrate in 200 ml of water was added. The reaction was carried out by following the procedure of Example 1. The results are shown in Table 1.

Control 1

Figure 7:
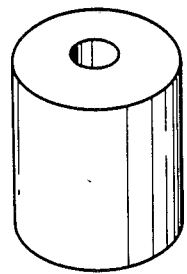
FIG. 7 is a perspective view of a Raschig ring carrier.
Figure 8:
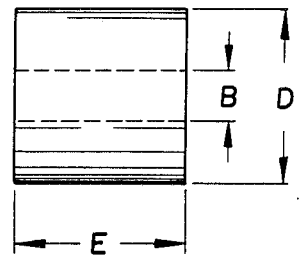
FIG. 8 is a front view of the Raschig ring carrier.
Figure 9:
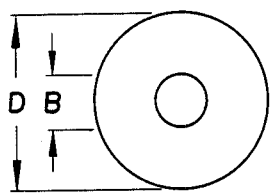
FIG. 9 is a side view of the Raschig ring carrier.

A catalyst was prepared by following the procedure of Example 1, except that an α-alumina carrier (FIGS. 7 to 9) in the shape of Raschig rings having a ratio of apparent surface area to apparent volume of 1.3 mm$^{-1}$, an outside diameter (D) of 7.0 mm, an inside diameter (B) of 3.0 mm, and a length (E) of 7.0 mm was used in the place of the carrier in the shape of Intalox saddles and a solution of 3.7 g of cesium nitrate in 740 ml of water was added. The reaction was also carried out by following the procedure of Example 1. The results are shown in Table 1.

Control 2

Figure 10:
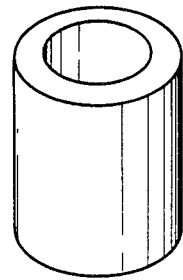
FIG. 10 is a perspective view of a Raschig ring carrier.
Figure 11:
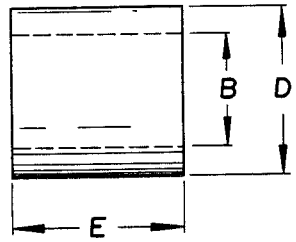
FIG. 11 is a front view of the Raschig ring carrier.
Figure 12:
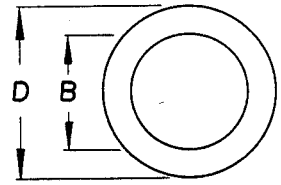
FIG. 12 is a side view of the Raschig ring.

A catalyst was prepared by following the procedure of Example 1, except that an α-alumina carrier (FIGS. 10 to 12) in the shape of Raschig rings having a ratio of apparent surface area to apparent volume of 2.1 mm$^{-1}$, an outside diameter (D) of 7.0 mm, an inside diameter (B) of 4.8 mm, and a length (E) of 7.0 mm was used in the place of the carrier in the shape of Intalox saddles and a solution of 2.3 g of cerium nitrate in 100 ml of water was added. The reaction was also carried out by following the procedure of Example 1. The results are shown in Table 1.

Control 3

A catalyst was prepared by following the procedure of Example 1, except that an α-alumina carrier in the shape of spheres (3.2 mm in diameter) having a ratio of apparent surface area to apparent volume of 1.9 mm$^{-1}$ was used in the place of the carrier in the shape of Intalox saddles and a solution of 4.4 g of cesium nitrate in 900 ml was added. The reaction was also carried out by following the procedure of Example 1. The results are shown in Table 1.

Control 4

A catalyst was prepared by following the procedure of Example 1.

The reaction was also carried out by following the procedure of Example 1, except that ethylene dichloride was omitted. The results are shown in Table 1.

13

Control 5

A catalyst was prepared by following the procedure of Example 3.

The reaction was also carried out by following the procedure of Example 3, except that ethylene dichloride was omitted. The results are shown in Table 1.

14

EXAMPLE 5

A slurry of 1,440 g of silver oxalate in 300 ml of water and 1,240 ml of ethanol amine added thereto were thoroughly stirred for solution. The resultant solution and 300 ml of water added thereto were thoroughly stirred. The resultant diluted solution and a solution of 21.5 g of

TABLE 1

| | Physical properties of porous inorganic carrier | | | | | | Cesium nitrate g · eg./kg catalyst | Silver deposition ratio (% by weight) | Ethylene dichloride (ppm) | Results of reaction | | | |
|---|---|---|---|---|---|---|---|---|---|---|---|---|---|
| | Pore volume (cc/g) | Specific surface area (m²/g) | Packed Specific gravity (kg/l) | Note 4 (mm⁻¹) | Shape | FIG. | | | | Reaction temperature (°C.) | Conversion (%) | Selectivity (%) | Pressure loss (kg/cm²) |
| Example | | | | | | | | | | | | | |
| 1 | 0.32 | 0.7 | 0.55 | 1.9 | Note 1 | 1-3 | $4.8 \times 10^{-3}$ | 10.4 | 1 | 222 | 7.0 | 81.2 | 0.3 |
| 2 | 0.32 | 0.7 | 0.55 | 1.9 | Note 1 | 1-3 | $1.5 \times 10^{-2}$ | 10.4 | 1 | 212 | 7.0 | 81.7 | 0.3 |
| 3 | 0.28 | 0.7 | 0.64 | 1.9 | Note 2 | 4-6 | $4.9 \times 10^{-3}$ | 9.1 | 1 | 221 | 7.0 | 81.3 | 0.3 |
| Control | | | | | | | | | | | | | |
| 1 | 0.35 | 0.7 | 0.88 | 1.3 | Note 3 | 7-9 | $4.9 \times 10^{-3}$ | 6.8 | 1 | 220 | 7.0 | 80.3 | 0.5 |
| 2 | 0.27 | 0.7 | 0.55 | 2.1 | Note 3 | 10-12 | $4.8 \times 10^{-3}$ | 10.4 | 1 | 229 | 7.0 | 80.3 | 0.3 |
| 3 | 0.33 | 0.7 | 1.06 | 1.9 | Spheres | — | $5.1 \times 10^{-3}$ | 5.7 | 1 | 218 | 7.0 | 79.8 | 1.8 |
| 4 | 0.32 | 0.7 | 0.55 | 1.9 | Note 1 | 1-3 | $4.8 \times 10^{-3}$ | 10.4 | 0 | 217 | 7.0 | 79.3 | 0.3 |
| 5 | 0.28 | 0.7 | 0.64 | 1.9 | Note 2 | 4-6 | $4.9 \times 10^{-3}$ | 9.1 | 0 | 216 | 7.0 | 79.3 | 0.3 |

Note 1: Intalox saddles
Note 2: Berl saddles
Note 3: Raschig rings
Note 4: Ratio of apparent surface area/apparent volume

EXAMPLE 4

A slurry of 1,440 g of silver oxalate in 300 ml of water and 1,240 ml of ethanol amine added thereto were thoroughly stirred for solution. The resultant solution and 300 ml of water added thereto were thoroughly stirred. In the resultant diluted solution, a solution of 22.4 g of cesium nitrate in 500 ml of water was stirred. Consequently, there was prepared an impregnating solution. With this impregnating solution, 9,000 ml of an α-alumina carrier (FIGS. 1 to 3) in the shape of Intalox saddles having an apparent porosity of 60%, a BET specific surface area of 0.7 m²/g, a pore volume of 0.40 cc/g, an outside diameter (D) of 6.0 mm, a thickness (W) of 2.0 mm, an outer peripheral length (A) of 13.3 mm, an inner peripheral length (C) of 5.8 mm, a length (E) of 10.0 mm, and a ratio of apparent surface area to apparent volume of 1.7 mm⁻¹ and preheated to about 100° C. was impregnated. The impregnated carrier was concentrated and dried by heating, further heated in a bath of air at 120°0 C. for three hours, and subsequently activated in a current of air at 280° C. for 48 hours.

The catalyst thus obtained was placed to pack a tightly closed container of stainless steel adapted to introduce an inert gas from outside. In an electric furnace under continued flow of nitrogen gas, the catalyst bed was heated at 630° C. for three hours.

The catalyst was placed to pack an externally heating double-pipe stainless steel reactor 33 mm in inside diameter and 10,000 mm in catalyst bed length. To the catalyst bed so produced, a mixed gas comprising 20% by volume of ethylene, 7% by volume of oxygen, 7% by volume of carbon dioxide gas, and the balance of methane, nitrogen, argon, and ethane and further containing 3 ppm of ethylene dichloride was introduced, to be subjected to the reaction at a reaction pressure of 24 kg/cm² G and a space velocity of 5,500 hr⁻¹ for 30 days. The results of the reaction are shown in Table 2.

cesium nitrate in 400 ml of water added thereto were stirred, to prepare an impregnating solution. With this impregnating solution, 9,000 ml of an α-alumina carrier (FIGS. 4 to 6) in the shape of Berl saddles having an apparent porosity of 60%, a BET specific surface area of 0.7 m²/g, a pore volume of 0.40 cc/g, an outside diameter (D) of 6.0 mm, thickness (W) of 2.0 mm, an outer peripheral length (A) of 15.4 mm, an inner peripheral length (C) of 6.2 mm, and a ratio of apparent surface area to apparent volume of 1.7 mm⁻¹ and preheated to about 100° C. was impregnated. The impregnated carrier was concentrated and dried by heating, and further heated in a bath of air at 120° C. for three hours, and then activated in a current of air at 280° C. for 48 hours.

The catalyst so produced was placed to pack a closed container of stainless steel adapted to introduce an inert gas from outside and, in an electric furnace under continued flow of nitrogen gas, heated for three hours, with the temperature of the catalyst bed kept at 630° C. The reaction using this catalyst was carried out by following the procedure of Example 4. The results are shown in Table 2.

EXAMPLE 6

A slurry of 1,440 g of silver oxalate in 300 ml of water and 1,240 ml of ethanol amine added thereto were thoroughly stirred for solution. The resultant solution and 300 ml of water added thereto were thoroughly stirred. The resultant diluted solution and a solution of 10.0 g of cesium nitrate in 500 ml of water added thereto were stirred, to prepare an impregnating solution. With this impregnating solution, 9,000 ml of an α-alumina carrier (FIGS. 1 to 3) in the shape of Intalox saddles having an apparent porosity of 60%, a BET specific surface area of 0.7 m²/g, a pore volume of 0.40 cc/g, an outside diameter (D) of 6.0 mm, a thickness (W) of 2.0 mm, an outer peripheral length (A) of 13.3 mm, an inner peripheral length (C) of 5.8 mm a length (E) of 10.0 mm, and a ratio of apparent surface area to apparent volume of 1.7 mm$^{-1}$ and preheated to about 100° C. was impregnated. The impregnated carrier was concentrated and dried by heating, then heated in a bath of air at 120° C. for three hours, and subsequently activated in a current of air at 280° C. for 48 hours.

The catalyst so produced was placed to pack a closed container of stainless steel adapted to introduced an inert gas from outside and, in an electric furnace under continued flow of nitrogen gas, was heated for three hours, with the temperature of the catalyst bed kept at 570° C. The reaction using this catalyst was carried out by following the procedure of Example 4. The results are shown in Table 2.

EXAMPLE 7

A slurry of 1,440 g of silver oxalate in 300 ml of water and 1,240 ml of ethanol amine added thereto were thoroughly stirred for solution. The resultant solution and 300 ml of water added thereto were thoroughly stirred. The resultant diluted solution and a solution of 46.5 g rubidium sulfate in 500 ml of water added thereto were stirred, to prepare an impregnating solution.

With this impregnating solution, 9,000 ml of an alumina carrier (FIGS. 1 to 3) in the shape of Intalox saddles having an apparent porosity of 60%, a BET specific surface area of 0.7 m$^2$/g, a pore volume of 0.40 cc/g, an outside diameter (D) of 6.0 mm, a length (E) of 10.0 mm, a thickness (W) of 2.0 mm, an outer peripheral length (A) of 13.3 mm, an inner peripheral length (C) of 5.8 mm, and a ratio of apparent surface area to apparent volume of 1.7 mm$^{-1}$ and preheated to about 100° C. was impregnated. The impregnated carrier was concentrated and dried by heating, then heated in a bath of air at 120° C. for three hours, and subsequently activated in a current of air at 280° C. for 48 hours.

The catalyst so produced was placed to pack a closed container of stainless steel adapted to introduced an inert gas from outside and, in an electric furnace under continued flow of nitrogen gas, was heated for three hours, with the temperature of the catalyst bed kept at 630° C. The reaction using this catalyst was carried out by following the procedure of Example 4. The results are shown in Table 2.

EXAMPLE 8

A slurry of 1,440 g of silver oxalate in 300 ml of water and 1,240 ml of ethanol amine added thereto were thoroughly stirred for solution. The resultant solution and 300 ml of water added thereto were thoroughly stirred. The resultant diluted solution and a solution of 19.4 g of potassium nitrate in 500 ml of water added thereto were stirred, to prepare an impregnating solution.

With this impregnating solution, 9,000 ml of an α-alumina carrier (FIGS. 1 to 3) in the shape of Intalox saddles having an apparent porosity of 60%, a BET specific surface area of 0.7 m$^2$/g, a pore volume of 0.40 cc/g, an outside diameter (D) of 6.0 mm, a thickness (W) of 2.0 mm, an outer peripheral length (A) of 13.3 mm, an inner peripheral length (C) of 5.8 mm, a length (E) of 10.0 mm, and a ratio of apparent surface area to apparent volume of 1.7 mm$^{-1}$ and preheated to about 100° C. was impregnated. The impregnated carrier was concentrated and dried by heating, then heated in a bath of air at 120° C. for three hours, and subsequently activated in a current of air at 280° C. for 48 hours.

The catalyst so produced was placed to pack a closed container of stainless steel adapted to introduced an inert gas from outside and, in an electric furnace under continued flow of nitrogen gas, was heated for three hours, with the temperature of the catalyst bed kept at 630° C. The reaction using this catalyst was carried out by following the procedure of Example 4. The results are shown in Table 2.

Control 6

A slurry of 1,440 g of silver oxalate in 300 ml of water and 1,240 ml of ethanol amine added thereto were thoroughly stirred for solution. The resultant solution and 600 ml of water added thereto were thoroughly stirred. The resultant diluted solution and a solution of 25.0 g of cesium nitrate in 500 ml of water added thereto were stirred, to prepare an impregnating solution. With this impregnating solution, 9,000 of an α-alumina carrier (FIGS. 7 to 9) in the shape of Raschig rings having an apparent porosity of 60%, a BET specific surface area of 0.7 m$^2$/g, a pore volume of 0.40 cc/g, a ratio of apparent surface area to apparent volume of 1.3 mm$^{-1}$, an outside diameter (D) of 7.0 mm, an inside diameter (B) of 3.0 mm, and a length (E) of 7.0 mm and preheated to about 100° C. was impregnated. The impregnated carrier was concentrated and dried by heating, then heated in a bath of air at 120°0 C. for three hours, and subsequently activated in a current of air at 280° C. for 48 hours.

The catalyst so produced was placed to pack a closed container of stainless steel adapted to introduce an inert gas from outside and, in an electric furnace under continued flow of nitrogen gas, was heated for three hours, with the temperature of the catalyst bed kept at 620° C. . The reaction using this catalyst was carried out by following the procedure of Example 4. The results are shown in Table 2.

Control 7

A slurry of 1,440 g of silver oxalate in 300 ml of water and 1,240 ml of ethanol amine added thereto were thoroughly stirred for solution. The resultant solution and 1,600 ml of water added thereto were thoroughly stirred. The resultant diluted solution and a solution of 33.1 g of cesium nitrate in 500 ml of water added thereto were stirred, to prepare an impregnating solution. With this impregnating solution, 9,000 ml of an α-alumina carrier in the shape of spheres (3.5 mm in diameter) having an apparent porosity of 60%, a BET specific surface area of 0.7 m$^2$/g, a pore volume of 0.40 cc/g, and a ratio of apparent surface area to apparent volume of 1.7 mm$^{-1}$ and preheated to about 100° C. was impregnated. The impregnated carrier was concentrated and dried by heating, then heated in a bath of air at 120° C. for three hours, and subsequently activated in a current of air at 280° C. for 48 hours.

The catalyst so produced was placed to pack a closed container of stainless steel adapted to introduce an inert gas from outside and, in an electric furnace under continued flow of nitrogen gas, was heated for three hours, with the temperature of the catalyst bed kept at 590° C. The reaction using this catalyst was carried out by following the procedure of Example 4. The results are shown in Table 2.

Control 8

A slurry of 1,440 g of silver oxalate in 300 ml of water and 1,240 ml of ethanol amine added thereto were thoroughly stirred for solution. The resultant solution and 50 ml of water added thereto were thoroughly stirred.

ried out by following the procedure of Control 9. The results are shown in Table 2.

TABLE 2

|  | Example | | | | | Control | | | | |
| --- | --- | --- | --- | --- | --- | --- | --- | --- | --- | --- |
|  | 4 | 5 | 6 | 7 | 8 | 6 | 7 | 8 | 9 | 10 |
| (Carrier) | | | | | | | | | | |
| Specific surface area (m$^2$/g) | 0.70 | 0.70 | 0.70 | 0.70 | 0.70 | 0.70 | 0.70 | 0.70 | 0.70 | 0.70 |
| Pore volume (cc/g) | 0.40 | 0.40 | 0.40 | 0.40 | 0.40 | 0.40 | 0.40 | 0.40 | 0.40 | 0.40 |
| Packed specific gravity (kg/liter) | 0.66 | 0.63 | 0.66 | 0.66 | 0.66 | 0.75 | 1.03 | 0.59 | 0.66 | 0.63 |
| Apparent porosity (%) | 60 | 60 | 60 | 60 | 60 | 60 | 60 | 60 | 60 | 60 |
| Shape | Intalox saddle | Berl saddle | Intalox saddle | Intalox saddle | Intalox saddle | Raschig ring | Sphere | Raschig ring | Intalox saddle | Berl saddle |
| $\frac{\text{Apparent surface area}}{\text{Apparent volume}}$ (mm$^{-1}$) | 1.7 | 1.7 | 1.7 | 1.7 | 1.7 | 1.3 | 1.7 | 1.7 | 1.7 | 1.7 |
| (Catalyst) | | | | | | | | | | |
| Silver deposition ratio (% by weight) | 14.0 | 14.6 | 14.0 | 14.0 | 14.0 | 12.5 | 9.4 | 15.4 | 14.0 | 14.6 |
| Alkali metal | Cesium | Cesium | Cesium | Rubidium | Potassium | Cesium | Cesium | Cesium | Cesium | Cesium |
| Alkali metal deposition ratio (equivalent/kg of catalyst) | 0.0165 | 0.0165 | 0.0074 | 0.0500 | 0.0275 | 0.0165 | 0.0165 | 0.0165 | 0.0165 | 0.0165 |
| High-temperature heated gas | Nitrogen | Nitrogen | Nitrogen | Nitrogen | Nitrogen | Nitrogen | Nitrogen | Nitrogen | Nitrogen | Nitrogen |
| High-temperature heating temperature (°C.) | 630 | 630 | 570 | 630 | 630 | 620 | 590 | 640 | 630 | 630 |
| High-temperature heating time (hours) | 3.0 | 3.0 | 3.0 | 3.0 | 3.0 | 3.0 | 3.0 | 3.0 | 3.0 | 3.0 |
| (Reaction) | | | | | | | | | | |
| Ethylene dichloride (ppm) | 3 | 3 | 3 | 3 | 3 | 3 | 3 | 3 | 0 | 0 |
| Reaction temperature (°C.) | 230 | 232 | 233 | 236 | 232 | 229 | 228 | 279 | 217 | 218 |
| Conversion (%) | 13 | 13 | 13 | 13 | 13 | 13 | 13 | 13 | 13 | 13 |
| Selectivity (%) | 81.0 | 80.8 | 80.9 | 79.0 | 78.0 | 80.8 | 79.8 | 79.8 | 78.0 | 77.9 |
| Pressure loss (kg/cm$^2$) | 1.1 | 0.9 | 1.1 | 1.1 | 1.1 | 1.5 | 4.8 | 1.0 | 1.1 | 0.9 |

The resultant diluted solution and a solution of 19.7 g of cesium nitrate in 500 ml of water added thereto were stirred, to prepare an impregnating solution. With this impregnating solution, 9,000 ml of an α-alumina carrier (FIGS. 10 to 12) in the shape of Raschig rings having an apparent porosity of 60%, a BET specific surface area of 0.7 m$^2$/g, a pore volume of 0.40 cc/g, a ratio of apparent surface area to apparent volume of 1.7 mm$^{-1}$, an outside diameter (D) of 7.0 mm, an inside diameter (B) of 4.2 mm, and a length (E) of 7.0 mm and preheated to about 100° C. was impregnated. The impregnated carrier was concentrated and dried by heating, then heated in a bath of air at 120° C. for three hours, and subsequently activated in a current of air at 280° C. for 48 hours.

The catalyst so produced was placed to pack a closed container of stainless steel adapted to introduced an inert gas from outside and, in an electric furnace under continued flow of nitrogen gas, was heated for three hours, with the temperature of the catalyst bed kept at 640° C. The reaction using this catalyst was carried out by following the procedure of Exmaple 4. The results are shown in Table 2.

Control 9

A catalyst was prepared by following the procedure of Example 4.

The reaction was also carried out by following the procedure of Example 4, except that ethylene dichloride was omitted. The results of the reaction are shown in Table 2.

Control 10

A catalyst was prepared by following the procedure of Example 5. The reaction using this catalyst was carried out by following the procedure of Control 9. The results are shown in Table 2.

EXAMPLE 9

A silver impregnating solution was prepared by dissolving 1,600 g of silver nitrate in 1.8 liters of monoethylene glycol and thoroughly stirring the resultant solution with 636 g of formamide added thereto.

With the impregnating solution, 9,000 ml of the same carrier as used in Example 4 was impregnated. The resultant mixture of impregnation was gradually heated to 130° C., stirred at this temperature for two hours, then heated to 160° C., and further stirred at this temperature for two hours to effect dispersion and deposition of reduced silver on the carrier. The silver-deposited catalyst consequently obtained was washed several times by boiling in 9,000 ml of water and then dried at 90° to 100° C. Then, the dried catalyst was impregnated with a solution of 4.52 g of cesium carbonate in 2,400 ml of ethyl alcohol. The silver-deposited catalyst so produced was dried at 80° to 100° C. The reaction using this catalyst was carried out by following the procedure of Example 4. The results are shown in Table 3.

EXAMPLE 10

A silver impregnating solution was prepared by dissolving 1,600 g of silver nitrate in 1.7 liters of monoethylene glycol and thoroughly stirring the resultant solution with 636 g of formamide added thereto.

With the impregnating solution, 9,000 ml of an α-alumina carrier (FIGS. 4 to 6) in the shape of Berl saddles having an apparent porosity of 60%, a BET specific surface area of 0.7 m$^2$/g, a pore volume of 0.40 cc/g, an outside diameter (D) of 6.0 mm, a thickness (W) of 2.0 mm, an outer peripheral length (A) of 15.4 mm, an inner peripheral length (C) of 6.2 mm, and a ratio of apparent surface area to apparent volume of 1.7 mm$^{-1}$ and preheated to about 100° C. was impregnated.

The resultant mixture of impregnation was gradually heated to 130° C., stirred at this temperature for two hours, then gradually heated to 160° C., and further stirred at this temperature for two hours to effect dispersion and deposition of reduced silver on the carrier. The silver-deposited catalyst consequently obtained was washed several times by boiling in 9,000 ml of water and then dried at 90° 1 to 100° C. Then, the dried catalyst was impregnated with a solution of 4.31 g of cesium carbonate in 2,300 ml of ethyl alcohol. The silver-deposited catalyst so produced was dried at 80° to 100° C. The reaction using this catalyst was carried out by following the procedure of Example 4. The results are shown in Table 3.

EXAMPLE 11

A silver impregnating solution was prepared by dissolving 1,600 g of silver nitrate in 1.8 liters of monoethylene glycol and thoroughly stirring the resultant solution with 636 g of formamide added thereto.

With the impregnating solution, 9,000 ml of the same carrier as used in Example 4 was impregnated. The resultant mixture of impregnation was gradually heated to 130° C., stirred at this temperature for two hours, then heated to 160° C., and further stirred at this temperature for two hours to effect dispersion and deposition of reduced silver on the carrier. The silver-deposited catalyst consequently obtained was washed several times by boiling in 9,000 ml of water and then dried at 90° to 100° C. Then, the dried catalyst was impregnated with a solution of 9.61 g of rubidium carbonate in 2,400 ml of ethyl alcohol. The silver-deposited catalyst so produced was dried at 80° to 100° C. The reaction using this catalyst was carried out by following the procedure of Example 4. The results are shown in Table 3.

EXAMPLE 12

A silver impregnating solution was prepared by dissolving 1,600 g of silver nitrate in 1.8 liters of monoethylene glycol and thoroughly stirring the resultant solution with 636 g of formamide added thereto.

With the impregnating solution, 9,000 ml of an α-alumina carrier (FIGS. 1 to 3) in the shape of Intalox saddles having an apparent porosity of 60%, a BET specific surface area of 0.7 m²/g, a pore volume of 0.40 cc/g, an outside diameter (D) of 6.0 mm, a thickness (W) of 2.0 mm, an outer peripheral length (A) of 13.3 mm, an inner peripheral length (C) of 5.8 mm a length (E) of 10.0 mm, and a ratio of apparent surface area to apparent volume of 1.7 mm$^{-1}$ and preheated to about 100° C. was impregnated. The resultant mixture of impregnation was gradually heated to 130° C., stirred at this temperature for two hours, then gradually heated to 160° C., and further stirred at this temperature for two hours to effect dispersion and deposition of reduced silver on the carrier. The silver-deposited catalyst consequently obtained was washed several times by boiling in 9,000 ml of water and then dried at 90° to 100° C. Then, the dried catalyst was impregnated with a solution of 4.51 g of potassium acetate in 2,400 ml of ethyl alcohol. The silver-deposited catalyst so produced was dried at 80° to 100° C. The reaction using this catalyst was carried out by following the procedure of Example 4. The results are shown in Table 3.

Control 11

A silver impregnating solution was prepared by dissolving 1,600 g of silver nitrate in 2.14 liters of monoethylene glycol and thoroughly stirring the resultant solution with 636 g of formamide added thereto. With the impregnating solution, 9,000 ml of an α-alumina carrier (FIGS. 7 to 9) in the shape of Raschig rings having an apparent porosity of 60%, a BET specific surface area of 0.7 m²/g, a pore volume of 0.40 cc/g, a ratio of apparent surface area to apparent volume of 1.3 mm$^{-1}$, an outside diameter (D) of 7.0 mm, an inside diameter (B) of 3.0 mm, and a length (E) of 7.0 mm, and preheated to about 100° C. was impregnated. The resultant mixture of impregnation was gradually heated to 130° C., stirred at this temperature for two hours, then heated to 160° C., and further stirred at this temperature for two hours to effect dispersion and deposition of reduced silver on the carrier. The silver-deposited catalyst consequently obtained was washed several times by boiling in 9,000 ml of water and then dried at 90° to 100° C. Then, the dried catalyst was impregnated with a solution of 5.13 g of cesium carbonate in 2,700 ml of ethyl alcohol. The silver-deposited catalyst so produced was dried at 80° to 100° C. The reaction using this catalyst was carried out by following the procedure of Example 4. The results are shown in Table 3.

Control 12

A silver impregnating solution was prepared by dissolving 1,600 g of silver nitrate in 3.14 liters of monoethylene glycol and thoroughly stirring the resultant solution with 636 g of formamide added thereto. With the impregnating solution, 9,000 ml of an α-alumina carrier in the shape of spheres (3.5 mm in diameter) having an apparent porosity of 60%, a BET specific surface area of 0.7 m²/g, a pore volume of 0.40 cc/g, a ratio of apparent surface area to apparent volume of 1.7 mm$^{-1}$ and preheated to about 100° C. was impregnated. The resultant mixture of impregnation was gradually heated to 130° C., stirred at this temperature for two hours, then heated to 160° C., and further stirred at this temperature for two hours to effect dispersion and deposition of reduced silver on the carrier. The silver-deposited catalyst consequently obtained was washed several times by boiling in 9,000 ml of water and then dried at 90° to 100° C. Then, the dried catalyst was impregnated with a solution of 7.05 g of cesium carbonate in 3,700 ml of ethyl alcohol. The silver-deposited catalyst so produced was dried at 80° to 100° C. The reaction using this catalyst was carried out by following the procedure of Example 4. The results are shown in Table 3.

Control 13

A silver impregnating solution was prepared by dissolving 1,600 g of silver nitrate in 1.56 liters of monoethylene glycol and thoroughly stirring the resultant solution with 636 g of formamide added thereto. With the impregnating solution, 9,000 ml of an α-alumina carrier (FIGS. 10 to 12) in the shape of Raschig rings having an apparent porosity of 60%, a BET specific surface area of 0.7 m²/g, a pore volume of 0.40 cc/g, a ratio of apparent surface area to apparent volume of 1.7 mm$^{-1}$, an outside diameter (D) of 7.0 mm, an inside diameter (B) of 4.2 mm, and a length (E) of 7.0 mm, and preheated to about 100° C. was impregnated. The resultant mixture of impregnation was gradually heated to 130° C., stirred at this temperature for two hours, then heated to 160° C., and further stirred at this temperature for two hours to effect dispersion and deposition of reduced silver on the carrier. The silver-deposited catalyst consequently obtained was washed several times by boiling in 9,000 ml of water and then dried at 90° to 100° C. Then, the dried catalyst was impregnated with a solution of 4,04 g of cesium carbonate in 2,130 ml of ethyl alcohol. The silver-deposited catalyst so produced was dried at 80° to 100° C. The reaction using this catalyst was carried out by following the procedure of Example 4. The results are shown in Table 3.

Control 14

A catalyst was prepared by following the procedure of Example 9.

The reaction was also carried out by following the procedure of Control 9. The results of the reaction are shown in Table 3.

Control 15

A catalyst was prepared by following the procedure of Example 10.

The reaction was also carried out by following the procedure of Control 9. The results of the reaction are shown in Table 3.

TABLE 3

| | Example | | | | Control | | | | |
|---|---|---|---|---|---|---|---|---|---|
| | 9 | 10 | 11 | 12 | 11 | 12 | 13 | 14 | 15 |
| (Carrier) | | | | | | | | | |
| Specific surface area (m²/g) | 0.70 | 0.70 | 0.70 | 0.70 | 0.70 | 0.70 | 0.70 | 0.70 | 0.70 |
| Pore volume (cc/g) | 0.40 | 0.40 | 0.40 | 0.40 | 0.40 | 0.40 | 0.40 | 0.40 | 0.40 |
| Packed specific gravity (kg/liter) | 0.66 | 0.63 | 0.66 | 0.66 | 0.75 | 1.03 | 0.59 | 0.66 | 0.63 |
| Apparent porosity (%) | 60 | 60 | 60 | 60 | 60 | 60 | 60 | 60 | 60 |
| Shape | Intalox saddle | Berl saddle | Intalox saddle | Intalox saddle | Raschig ring | Sphere | Raschig ring | Intalox saddle | Berl saddle |
| Apparent surface area / Apparent volume (mm$^{-1}$) | 1.7 | 1.7 | 1.7 | 1.7 | 1.3 | 1.7 | 1.7 | 1.7 | 1.7 |
| (Catalyst) | | | | | | | | | |
| Silver deposition ratio (% by weight) | 13.9 | 14.6 | 13.9 | 13.9 | 12.5 | 9.5 | 15.4 | 13.9 | 14.6 |
| Alkali metal | Cesium | Cesium | Rubidium | Potassium | Cesium | Cesium | Cesium | Cesium | Cesium |
| Alkali metal deposition ratio (equivalent/kg of catalyst) | 0.0041 | 0.0041 | 0.012 | 0.0068 | 0.0041 | 0.0043 | 0.004 | 0.0041 | 0.0041 |
| (Reaction) | | | | | | | | | |
| Ethylene dichloride (ppm) | 3 | 3 | 3 | 3 | 3 | 3 | 3 | 0 | 0 |
| Reaction temperature (°C.) | 228 | 231 | 237 | 233 | 228 | 228 | 239 | 216 | 218 |
| Conversion (%) | 13 | 13 | 13 | 13 | 13 | 13 | 13 | 13 | 13 |
| Selectivity (%) | 80.7 | 80.6 | 78.3 | 78.0 | 79.8 | 79.6 | 79.7 | 77.6 | 77.5 |
| Pressure loss (kg/cm²) | 1.1 | 0.9 | 1.1 | 1.1 | 1.5 | 4.8 | 1.0 | 1.1 | 0.9 |

What is claimed is:

1. A silver catalyst having fine silver particles dispersed and deposited on the outer surface of a porous inorganic refractory carrier and on the inner wall surface of pores in said carrier and used for the production of ethylene oxide by catalytic vaporphase oxidation of ethylene with molecular oxygen in the presence of a halogenated inhibitor, having silver and at least one accelerator selected from the group consisting of alkali metals and alkali metal compounds deposited on said porous inorganic refractory carrier in the shape of Intalox saddles or Berl saddles, wherein said porous inorganic refractory carrier has a specific pore volume in the range of 0.06 to 1.0 cc/g, an outer peripheral length (A) in the range of 3 to 70 mm, an inner peripheral length (C) in the range of 1.5 to 68 mm, a thickness (W) in the range of 0.8 to 4 mm, an outside diameter (D) in the range of 0.5 to 20 mm, and a length (E) in the range of 0.5 to 65 mm.

2. A silver catalyst according to claim 1, wherein said porous inorganic refractory carrier has a specific surface area in the range of 0.01 to 10 m²/g.

3. A silver catalyst according to claim 1, wherein the ratio of apparent surface area to apparent volume in said porous inorganic refractory carrier falls in the range of 0.1 to 10 mm$^{-1}$.

4. A silver catalyst according to claim 1, wherein said porous inorganic refractory carrier has an apparent porosity in the range of 20 to 80%.

5. A silver catalyst according to claim 2, wherein the amount of silver deposited on said carrier is in the range of 5 to 30% by weight, based on said catalyst.

6. A silver catalyst according to claim 5, wherein the amount of said accelerator falls in the range of 0.001 to 0.05 gram equivalent per kg of the completed catalyst.

7. A silver catalyst according to claim 1, wherein said porous inorganic refractory carrier has a specific surface area in the range of 0.1 to 5 m²/g.

8. A silver catalyst according to claim 1, wherein the ratio of apparent surface area to apparent volume in said porous inorganic refractory carrier falls in the range of 0.5 to 5 mm$^{-1}$.

9. A silver catalyst according to claim 1, wherein said porous inorganic refractory carrier has an apparent porosity in the range of 30 to 70%.

10. A silver catalyst according to claim 1, wherein said porous inorganic refractory carrier is in the shape of Intalox saddles.

11. A silver catalyst according to claim 1, wherein said porous inorganic refractory carrier is in the shape of Berl saddles.

12. A silver catalyst according to claim 11, wherein said porous inorganic refractory carrier has a specific pore volume in the range of 0.06 to 1.0 cc/g, an outer peripheral length (A) in the range of 3 to 70 mm, an inner peripheral length (C) in the range of 1.5 to 68 mm, a thickness (W) in the range of 0.1 to 4 mm, an outside diameter (D) in the range of 0.5 to 20 mm, and a length (E) in the range of 0.5 to 65 mm.

13. A silver catalyst according to claim 1, wherein said alkali metal is at least one member selected from the group consisting of potassium, rubidium, and cesium.

14. A silver catalyst according to claim 13, wherein said alkali metal is cesium.

15. A method for the manufacture of a silver catalyst having fine silver particles dispersed and deposited on the outer surface of a porous inorganic refractory carrier and on the inner wall surface of pores in said carrier and used for the production of ethylene oxide by catalytic vapor phase oxidation of ethylene with molecular oxygen in the presence of a halogenated inhibitor, which method is characterized by causing silver and at least one accelerator selected from the group consisting of alkali metals and alkali metal compounds to be deposited on a porous inorganic refractory carrier in the shape of Intalox saddles or Berl saddles, wherein said porous inorganic refractory carrier has a specific pore volume in the range of 0.06 to 1.0 cc/g, an outer peripheral length (A) in the range of 3 to 70 mm, an inner peripheral length (C) in the range of 1.5 to 68 mm, a thickness (W) in the range of 0.8 to 4 mm, an outside diameter (D) in the range of 0.5 to 20 mm, and a length (E) in the range of 0.5 to 65 mm, and finally subjecting the resultant composite to a high temperature treatment in an inert gas having an oxygen content of not more than 3% by volume at a temperature in the range of 550° to 950° C.

16. A method according to claim 15, wherein said porous inorganic refractory carrier has a specific surface area in the range of 0.01 to 10 m$^2$/g.

17. A method according to claim 15, wherein the ratio of apparent surface area to apparent volume in said porous inorganic refractory carrier is in the range of 0.1 to 10 mm$^{-1}$.

18. A method according to calim 15, wherein said porous inorganic refractory carrier has an apparent porosity in the range of 20 to 80%.

19. A method according to claim 15, wherein the amount of silver deposited on said carrier is in the range of 5 to 30% by weight based on said catalyst.

20. A method according to claim 15, wherein the amount of said accelerator is in the range of 0.001 to 0.05 gram equivalent per kg of the completed catalyst.

21. A method according to claim 15, wherein said alkali metal is at least one member selected from the group consisting of potassium, rubidium, and cesium.

22. A method for the manufacture of a silver catalyst having fine silver particles dispersed and deposited on the outer surface of a porous inorganic refractory carrier and on the inner wall surface of pores in said carrier and used for the production of ethylene oxide by catalytic vapor phase oxidation of ethylene with molecular oxygen in the presence of a halogenated inhibitor, which method is characterized by causing silver and at least one accelerator selected from the group consisting of alkali metals and alkali metal compounds to be deposited on a porous inorganic refractory carrier in the shape of Intalox saddles or Berl saddles, wherein said porous inorganic refractory carrier has a specific pore volume in the range of 0.06 to 1.0 cc/g, an outer peripheral length (A) in the range of 3 to 70 mm, an inner peripheral length (C) in the range of 1.5 to 68 mm, a thickness (W) in the range of 0.8 to 4 mm, an outside diameter (D) in the range of 0.5 to 20 mm, and a length (E) in the range of 0.5 to 65 mm, with silver compound solution containing a reducing compound, heating the impregnated carrier for the reduction thereby dispersing and depositing metallic silver on the outer surface of the carrier and on the inner surface of pores in the carrier, subsequently washing the resultant composite with at least one liquid selected from the group consisting of water and lower alcohols, drying the wet composite, impregnating the dried composite with a solution containing at least one member selected from the group consisting of alkali metals and alkali metal compounds, and drying the wet composite thereby expelling the liquid component through vaporization.

23. A method according to claim 22, wherein said porous inorganic refractory carrier has a specific surface area in the range of 0.01 to 10 m$^2$/g.

24. A method according to claim 22, wherein the ratio of apparent surface area to apparent volume in said porous inorganic refractory carrier is in the range of 0.1 to 10 mm$^{-1}$.

25. A method according to claim 22, wherein said porous inorganic refractory carrier has an apparent porosity in the range of 20 to 80%.

26. A method according to claim 24, wherein the amount of silver deposited on said carrier is in the range of 5 to 30% by weight based on said catalyst.

27. A method according to claim 22, wherein the amount of said accelerator is in the range of 0.0001 to 0.03 gram equivalent per kg of the completed catalyst.

28. A method according to claim 22, wherein said alkali metal is at least one member selected from the group consisting of potassium, rubidium, and cesium.

* * * * *